US008553959B2

(12) United States Patent
Hsieh et al.

(10) Patent No.: US 8,553,959 B2
(45) Date of Patent: Oct. 8, 2013

(54) METHOD AND APPARATUS FOR CORRECTING MULTI-MODALITY IMAGING DATA

(75) Inventors: Jiang Hsieh, Brookfield, WI (US); James George Colsher, Durham, NC (US); Albert Henry Lonn, Beaconsfield (GB); Alexander Ganin, Whitefish Bay, WI (US); Jean-Baptiste Thibault, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 1128 days.

(21) Appl. No.: 12/053,370

(22) Filed: Mar. 21, 2008

(65) Prior Publication Data

US 2009/0238427 A1 Sep. 24, 2009

(51) Int. Cl.
*G06K 9/00* (2006.01)

(52) U.S. Cl.
USPC ............................................. 382/131

(58) Field of Classification Search
USPC ............. 382/128; 250/363.04, 336.1, 363.01, 250/363.02; 378/21, 23, 25, 26, 27; 600/436, 425
See application file for complete search history.

(56) References Cited

U.S. PATENT DOCUMENTS

| | | | |
|---|---|---|---|
| 5,341,460 A * | 8/1994 | Tam | 345/419 |
| 5,533,091 A * | 7/1996 | Hsieh | 378/210 |
| 5,663,566 A * | 9/1997 | Maniawski et al. | 250/369 |
| 6,211,523 B1 | 4/2001 | Gagnon | |
| 6,242,743 B1 | 6/2001 | DeVito et al. | |
| 6,399,951 B1 | 6/2002 | Paulus et al. | |
| 6,449,331 B1 | 9/2002 | Nutt et al. | |
| 6,670,614 B1 | 12/2003 | Plut et al. | |
| 6,720,812 B2 | 4/2004 | Tumer et al. | |
| 7,396,162 B1 * | 7/2008 | Edic et al. | 378/207 |
| 7,512,284 B2 * | 3/2009 | Avinash | 382/266 |
| 7,924,969 B2 * | 4/2011 | Yamakawa et al. | 378/5 |
| 2003/0105397 A1 * | 6/2003 | Tumer et al. | 600/436 |
| 2003/0128801 A1 | 7/2003 | Eisenberg et al. | |

(Continued)

FOREIGN PATENT DOCUMENTS

| | | |
|---|---|---|
| CN | 1140283 | 1/1997 |
| JP | 2000-102529 | 4/2000 |

OTHER PUBLICATIONS

"Attenuation correction for a PET by CT image", Li Xue-li, Zhaq Yong-je, (Proceedings of annual conference of CT an 3D imaging), pp. 24-26, Oct. 2004.

(Continued)

*Primary Examiner* — Robert Kim
*Assistant Examiner* — Jason McCormack
(74) *Attorney, Agent, or Firm* — The Small Patent Law Group; Dean D. Small (57) ABSTRACT

A method for correcting Positron Emission Tomography (PET) data includes adjusting a tube current generated by the CT imaging system to a second tube current value that is less than a first tube current value used to generate diagnostic quality CT images, and imaging the patient with the CT imaging system set at the second tube current value. The method also includes generating a plurality of computed tomography (CT) projection data from the CT imaging system and preprocessing the CT projection data to generate preprocessed CT projection data. The method further includes filtering the preprocessed CT projection data to reduce electronic noise to generate filtered CT projection data, and performing a minus logarithmic operation on the filtered CT projection data to generate the corrected PET data.

24 Claims, 4 Drawing Sheets

(56) References Cited

U.S. PATENT DOCUMENTS

| | | | |
|---|---|---|---|
| 2004/0030246 A1* | 2/2004 | Townsend et al. | 600/427 |
| 2004/0102688 A1* | 5/2004 | Walker et al. | 600/407 |
| 2005/0023471 A1 | 2/2005 | Wang et al. | |
| 2005/0135664 A1* | 6/2005 | Kaufhold et al. | 382/131 |
| 2005/0201635 A1* | 9/2005 | Mori | 382/274 |
| 2005/0276373 A1* | 12/2005 | Ying et al. | 378/7 |
| 2006/0013454 A1* | 1/2006 | Flewelling et al. | 382/128 |
| 2007/0019779 A1* | 1/2007 | Nishide et al. | 378/4 |
| 2007/0165943 A1* | 7/2007 | Guetter et al. | 382/159 |
| 2008/0123992 A1* | 5/2008 | Tian et al. | 382/276 |

OTHER PUBLICATIONS

State Intellectual Property Office of People's Republic of China Search Report and Office Action dated Oct. 24, 2012.

"CT vs Ge attenuation correction in a combined PET/CT system: evaluation of the effect of lowering the CT tube current", Ehab Kamel et al., Dec. 18, 2001.

\* cited by examiner

METHOD AND APPARATUS FOR CORRECTING MULTI-MODALITY IMAGING DATA

BACKGROUND OF THE INVENTION

This invention relates generally to imaging systems capable of operation in multiple modalities, and more particularly to an apparatus and method for correcting multi-modality imaging data.

Multi-modal imaging systems are capable of scanning using different modalities, such as, for example, but not limited to, Positron Emission Tomography (PET), Single photon emission computed tomography (SPECT), and Computed Tomography (CT). Conventional PET/CT imaging systems obtain CT images for attenuation correction in PET and to provide anatomical information to aid a physician in localizing tracer uptake used during PET imaging of a patient. In some cases, the CT diagnostic images are read separately. The accuracy of the reconstructed CT numbers is important to ensure adequate representation of the tracer uptake in the organ. Under normal scanning conditions, this constraint can be easily met by the CT imaging system because of the tight tolerances on the CT number uniformity requirement required of the CT reconstruction algorithm.

In multi-modality systems, for example, an integrated PET/CT system, the PET and CT images should be inherently registered with one another. Inherent registration arises when the detectors for the PET and CT imaging systems are physically mounted to a common frame. Conventional integrated PET/CT systems or SPECT/CT systems utilize data that is generated by the CT imaging system to generate attenuation correction information for the PET or SPECT scan data. Specifically, a plurality of emission attenuation correction factors is derived from CT data that is generated during a CT scan. The term CTAC is used to denote the map of emission attenuation coefficients that are derived from the CT images. The image quality of the CT diagnostic images far exceeds that required to generate the CTAC.

Additionally, patient motion induced imaging artifacts have become an increasingly important issue for PET attenuation correction. For example, since the CT images are typically acquired during a short time period, the attenuation map generated by the CT images represents the attenuation characteristics of the patient where there is little or no breathing motion. In contrast, the PET images are typically acquired over a relatively long time period where a patient is allowed to breathe freely due to the long acquisition time. The mismatch between the two data acquisition modes may result in image artifacts in the attenuation corrected PET images.

One known method for reducing the imaging artifacts is to average the CT image (or generate a maximum intensity CT image) of multiple respiratory phases to mimic the effect of the PET acquisition collected over multiple respiratory cycles. Another known method for reducing the imaging artifacts is to use respiratory gated CT acquisitions to generate attenuation correction maps that better match the respiratory characteristics of the respiratory gated PET acquisition. Typical protocols require a cine CT acquisition of 6-8 seconds with a respiratory motion-monitoring device. CT images of multiple respiratory phases are then reconstructed to match the corresponding phases in the respiratory gated PET acquisition.

Although each of the known methods is effective in reducing patient motion induced image artifacts, each known method also results in an increased X-ray radiation dosage being delivered to the patient as cine-CT scanning requires multiple consecutive exposures to x-ray over some extended period of time. Since, the resolution of the diagnostic CT images far exceeds the resolution required to generate the CTAC one method of reducing the X-ray radiation dosage is to reduce the X-ray tube current, i.e. to reduce the CT image resolution.

For example, when the X-ray tube current is set to a level that is sufficient to generate CT diagnostic images, the electronic noise is a small fraction of the fluctuation due to x-ray photon statistics and, therefore, does not significantly impact the final projection reading. However, when the X-ray tube current is reduced, thus reducing the x-ray flux, the electronic noise becomes a significant portion of the overall noise. As a result, as the X-ray tube current is decreased to reduce patient dosage, significant increases in image shading occurs and the CT number inaccuracies become more apparent. Additionally reducing the X-ray tube current below the level that is used to generate diagnostic CT images eventually results in CT images that are not acceptable for PET attenuation correction.

BRIEF DESCRIPTION OF THE INVENTION

In one embodiment, a method for correcting multi-modality imaging data is provided. The method includes adjusting a tube current generated by the CT imaging system to a tube current value that is less than a first tube current value used to generate diagnostic quality CT images, and imaging the patient with the CT imaging system set at the lower tube current value. The method also includes generating a plurality of computed tomography (CT) projection data, and preprocessing the CT projection data to generate preprocessed CT projection data. The method further includes filtering the preprocessed CT projection data, using a mean preserving filter, to reduce the effect of electronic noise and to generate filtered CT projection data, and performing a minus logarithmic operation on the filtered CT projection data to generate the corrected multi-modality imaging data. The method also includes generating a CT image that is used to generate attenuation correction factors for correcting PET data.

In another embodiment, a multi-modality imaging system including a first modality unit, a second modality unit, and a computer operationally coupled to the first and second modality units is provided. The computer is programmed to generate a plurality of computed tomography (CT) projection data, and preprocess the CT projection data to generate preprocessed CT projection data. The computer is also programmed to filter the preprocessed CT projection data to reduce the effect of electronic noise, and perform a minus logarithmic operation and other calibration steps on the filtered CT projection data to generate corrected multi-modality imaging data.

In a further embodiment, a computer readable medium encoded with a program programmed to instruct a computer is provided. The computer readable medium is programmed to generate a plurality of computed tomography (CT) projection data, and preprocess the CT projection data to generate preprocessed CT projection data. The computer readable medium is also programmed to filter the preprocessed CT projection data to reduce electronic noise to generate filtered CT projection data, and perform a minus logarithmic operation and other calibration steps on the filtered CT projection data to generate corrected multi-modality imaging data.

DETAILED DESCRIPTION OF THE INVENTION

Figure 1:
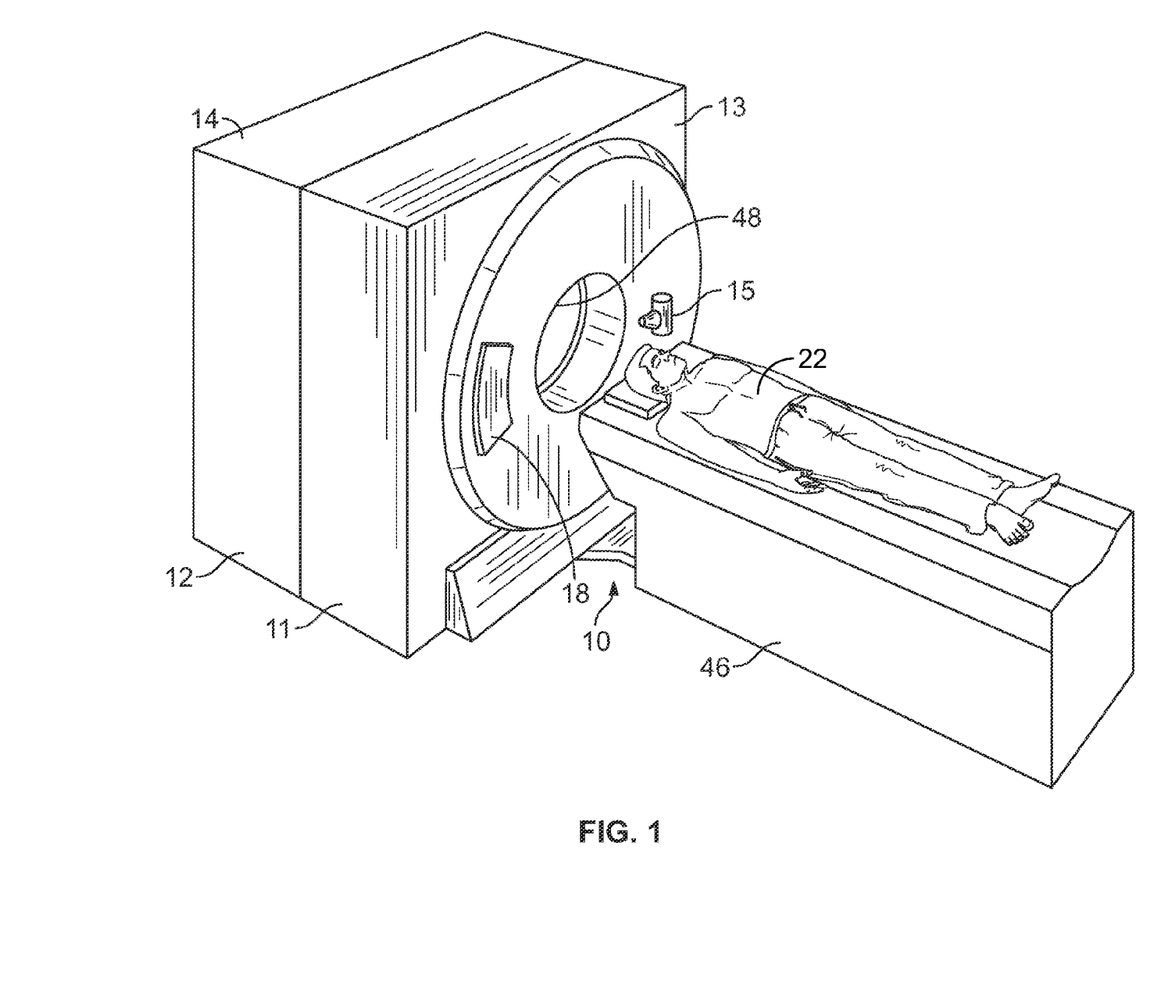
FIG. 1 is a pictorial view of an exemplary multi-modal imaging system in accordance with an embodiment of the present invention.
Figure 2:
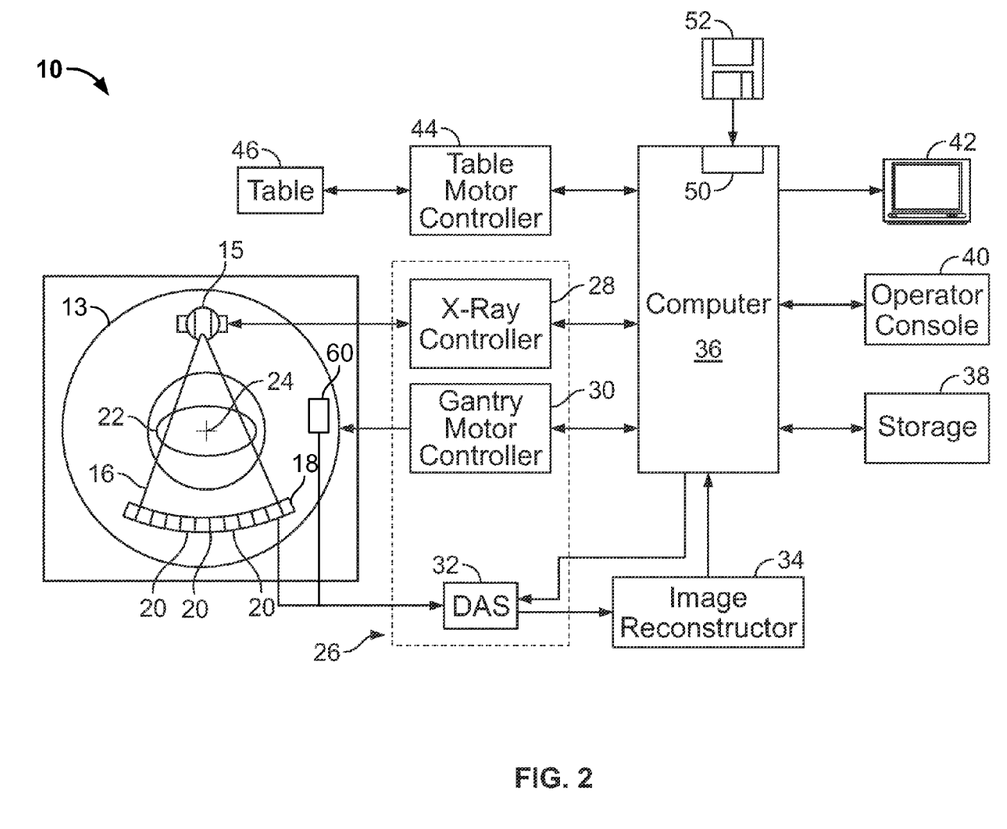
FIG. 2 is a block schematic diagram of the system illustrated in FIG. 1 in accordance with an embodiment of the present invention.

FIG. 1 is a pictorial view of an exemplary multi-modal imaging system 10 in accordance with an embodiment of the present invention. FIG. 2 is a block schematic diagram of the multi-modal imaging system 10 illustrated in FIG. 1 in accordance with an embodiment of the present invention. Although embodiments of the present invention are described in the context of an exemplary dual modality imaging system that includes a CT imaging system and a PET imaging system it should be understood that other imaging systems capable of performing the functions described herein are contemplated as being used.

There is herein provided a system and method for correcting multi-modality imaging data. The apparatus and methods are illustrated with reference to the figures wherein similar numbers indicate the same elements in all figures. Such figures are intended to be illustrative rather than limiting and are included herewith to facilitate explanation.

As discussed above, at least one known multi-modality system utilizes CT diagnostic quality images for both diagnostic purposes and to generate a plurality of attenuation correction factors that are derived from the CT data. In such multi-modality systems, such as, for example, an integrated PET/CT system there is an inherent registration of the PET and CT images the system acquires. Since the patient lies still on the same table during the PET and CT portions of the acquisition, the patient will be in a consistent position and orientation during the two acquisitions, greatly simplifying the process of correlating and fusing the CT and PET images. This allows the CT image to be used to provide attenuation correction information for the reconstruction of the PET image, and allows an image reader to easily correlate the anatomic information presented in the CT image and the functional information presented in the PET image. However, it is desirable to provide the attenuation information for the reconstruction of the PET image using an X-ray tube current that is less than the X-ray tube current utilized to generate the CT diagnostic quality images, or using an x-ray tube voltage that is lower than that utilized to generate diagnostic quality images. It is also desirable to reduce and/or eliminate the imaging artifacts that occur in the CT images when the X-ray tube current is reduced.

Referring to FIGS. 1 and 2, a multi-modal imaging system 10 is illustrated, and includes a first modality unit 11 and a second modality unit 12. The two modality units, 11 and 12, enable system 10 to scan an object or patient 22 in a first modality using the first modality unit 11 and to scan the object in a second modality using the second modality unit 12. System 10 allows for multiple scans in different modalities to facilitate an increased diagnostic capability over single modality systems. In one embodiment, multi-modal imaging system 10 is a Positron Emission Tomography/Computed Tomography (PET/CT) imaging system 10. Optionally modalities other than CT and PET are employed with system 10. The first modality unit 11, i.e. the CT imaging system includes a gantry 13 that has an x-ray source 15 that projects a beam of x-rays 16 toward a detector array 18 on the opposite side of gantry 13. Detector array 18 is formed by a plurality of detector rows that each include a plurality of detector elements 20 that together sense the projected x-rays that pass through an object, such as a medical patient 22. Each detector element 20 produces an electrical signal that represents the intensity of an impinging X-ray beam and hence allows estimation of the attenuation of the beam as it passes through object or patient 22. During a scan to acquire x-ray projection data, gantry 13 and the components mounted thereon rotate about a center of rotation 24. FIG. 2 shows only a single row of detector elements 20 (i.e., a detector row). However, a multislice detector array 18 includes a plurality of parallel detector rows of detector elements 20 such that projection data corresponding to a plurality of slices can be acquired simultaneously during a scan.

Rotation of gantry 13 and the operation of x-ray source 15 are governed by a control mechanism 26 of PET/CT system 10. Control mechanism 26 includes an x-ray controller 28 that provides power and timing signals to x-ray source 15 and a gantry motor controller 30 that controls the rotational speed and position of gantry 13. A data acquisition system (DAS) 32 in control mechanism 26 samples analog data from detector elements 20 and converts the data to digital signals for subsequent processing. An image reconstructor 34 receives the sampled and digitized x-ray data from DAS 32 and performs high-speed image reconstruction. The reconstructed image is applied as an input to a computer 36 that stores the image in a storage device 38. Computer 36 also receives commands and scanning parameters from an operator via console 40 that has a keyboard. An associated visual display unit 42 allows the operator to observe the reconstructed image and other data from computer.

The operator supplied commands and parameters are used by computer 36 to provide control signals and information to DAS 32, x-ray controller 28 and gantry motor controller 30. In addition, computer 36 operates a table motor controller 44 that controls a motorized table 46 to position patient 22 in gantry 13. Particularly table 46 moves at least a portion of patient 22 through a gantry opening 48.

In one embodiment computer 36 includes a device 50 for example a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

PET/CT system 10 also includes the second imaging modality 12, i.e. the PET imaging modality. The PET imaging modality 12 includes a PET emission detector 60 including a plurality of detector elements (not shown). The PET emission detector 60 and CT detector array 18 both detect radiation and are both referred to herein as radiation detectors. In one embodiment, PET/CT system 10 is a Discovery LS PET/CT system commercially available from General Electric Healthcare, Waukesha Wis., and configured as herein described. In another embodiment, the multi-modality imaging system 10 is a Hawkeye PET/SPECT/CT system also commercially available from GE Healthcare Waukesha Wis., and configured as herein described. Additionally, although described in a medical setting, it is contemplated that the benefits of the invention described herein may also accrue to all multi-modality imaging systems.

In the exemplary embodiment, the x-ray source 15 and the detector array 18 are rotated with a gantry 13 within the imaging plane and around the patient 24 to be imaged such that the angle at which the x-ray beam 16 intersects the patient 24 constantly changes. A group of x-ray attenuation measurements, i.e., projection data, from the detector array 18 at one gantry angle is referred to as a "view". A "scan" of the patient 24 comprises a set of views made at different gantry angles, or view angles, during one revolution of the x-ray source 15 and detector 18.

In a CT scan, the projection data is processed to construct an image that corresponds to a two dimensional slice taken through the patient 24. One method for reconstructing an image from a set of projection data is referred to in the art as the filtered back projection technique. This process converts the integral attenuation measurements into an image representing attenuation of the patient in each pixel. The attenuation measurements are typically converted into units of CT numbers or Hounsfield units.

To reduce the total scan time, a "helical" scan may be performed. To perform a "helical" scan, the patient 24 is moved while the data for the prescribed number of slices is acquired. Such a system generates a single helix from a fan beam helical scan. The helix mapped out by the fan beam yields projection data from which images in each prescribed slice may be reconstructed. Multiple helices are obtained using a multi-slice detector Reconstruction algorithms for helical scanning typically use helical weighing algorithms that weight the collected data as a function of view angle and detector channel index. Specifically prior to the filtered back projection process, the data is weighted according to a helical weighing factor that is a function of both the gantry angle and detector angle. The weighted data is then processed to generate CT numbers and to construct an image that corresponds to a two dimensional slice taken through the patient 24. During operation of multi-slice PET/CT system 10, multiple projections are acquired simultaneously faith multiple detector rows. Similar to the case of helical scan, weighting functions are applied to the projection data prior to the filtered back projection process.

During operation of the PET imaging system 19, positrons, i.e. positively charged electrons or anti-electrons, are emitted by radionuclides that have been prepared using a cyclotron or other device. The radionuclides most often employed in diagnostic imaging are fluorine-18 (18F), ruibidium-82 (82Rb), carbon-11 (11C), nitrogen-13 (13N), and oxygen-15 (15O). Radionuclides are employed as radioactive tracers called "radiopharmaceuticals" by incorporating them into substances such as glucose or carbon dioxide.

In typical use, the radiopharmaceutical is injected into a patient, such as patient 24, and accumulates in an organ, vessel or the like, that is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism fatty acid metabolism and protein synthesis.

After the radiopharmaceutical becomes concentrated within an organ of interest and while the radionuclides decay the radionuclides emit positrons. The positrons travel a very short distance before they encounter an electron and, when the positron encounters an electron, the positron is annihilated and converted into two photons. This annihilation event is characterized by two features that are pertinent to imaging and particularly to medical imaging using photon emission tomography (PET). First, each annihilation photon has an energy of approximately 511 keV upon annihilation. Second, the taco annihilation photons are directed in substantially opposite directions.

In PET imaging, if the general locations of annihilations can be identified in three dimensions, a three dimensional image of an organ of interest can be reconstructed for observation. To detect annihilation locations, a PET camera, such as emission detector 60 (shown in FIG. 2), for example, is employed. An exemplary PET camera includes a plurality of detectors and a processor that, among other things, includes coincidence detection circuitry.

The coincidence circuitry (not shown) identifies essentially simultaneous pulse pairs that correspond to detectors that are essentially on opposite sides of the imaging area. Thus, a simultaneous pulse pair indicates that an annihilation event has occurred on a straight line between an associated pair of detectors. Over an acquisition period of a few minutes, millions of annihilations are recorded, and each annihilation is associated with a particular detector pair via PET DAS 32, for example. After an acquisition period, recorded annihilation data can be used via any of several different well-known image reconstruction methods to construct the three dimensional image of the organ of interest.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

As described previously herein, PET/CT system 10 is configured to utilize data that is generated operating the CT modality of system 10 to generate attenuation correction factors that are utilized during operation of the PET modality of system 10. Specifically, the emission attenuation correction factors (CTAC) are derived from CT data that is generated during a CT scan, wherein the CT system is configured to generate CT data at a spacing and technique that produces the best CT image quality and to utilize the same CT projection data to generate an attenuation-corrected PET image.

During operation of PET/CT imaging system 10, a patient 24 is scanned to generate 102 a plurality of CT images. As discussed herein, the term "image" broadly refers to both viewable images and data representing a viewable image. The generated images are then utilized to generate the CT attenuation correction factors.

Figure 3A:
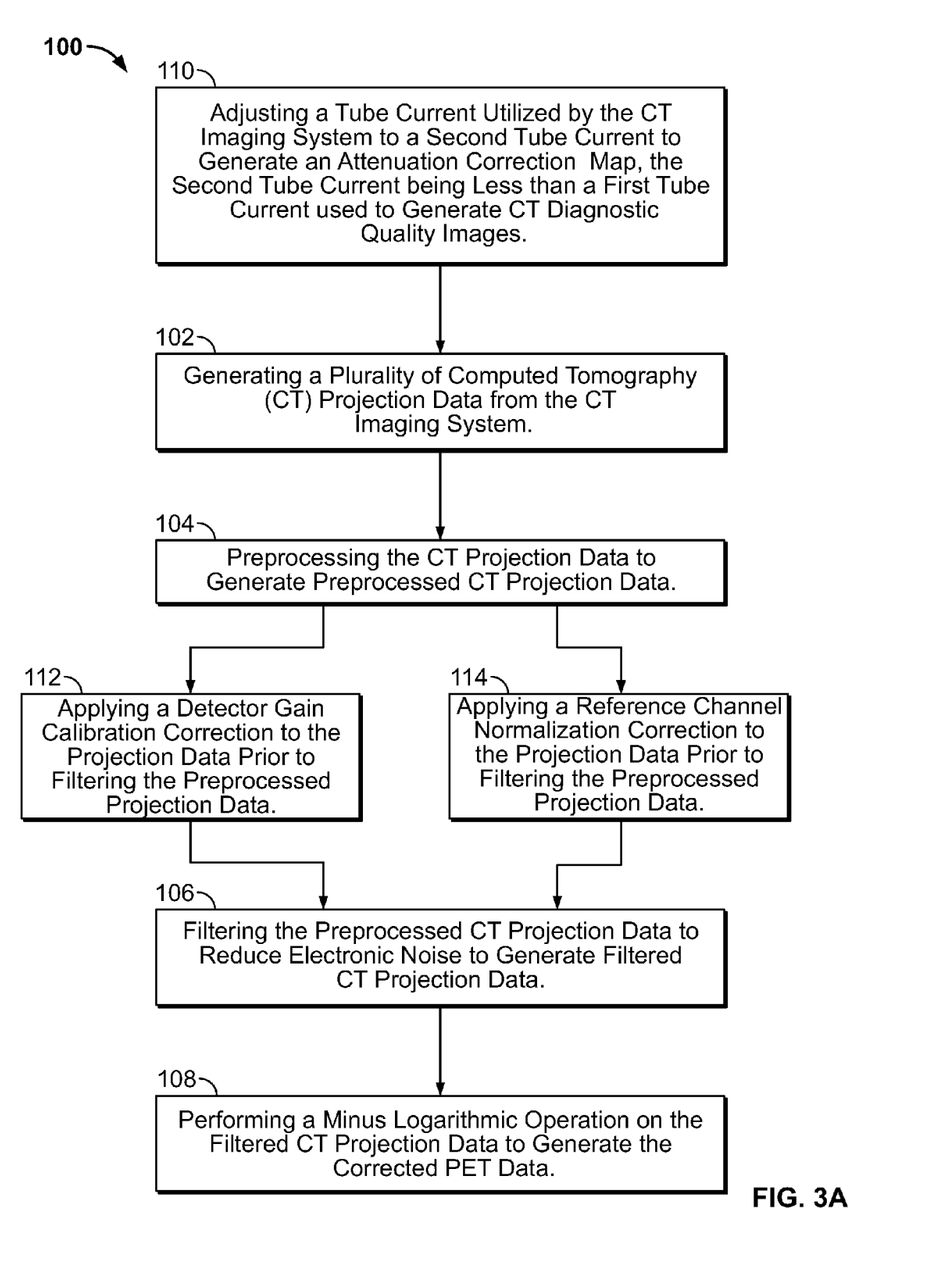
FIGS. 3A and 3B are flowcharts illustrating an exemplary method for correcting Positron Emission Tomography (PET) data.
Figure 3B:
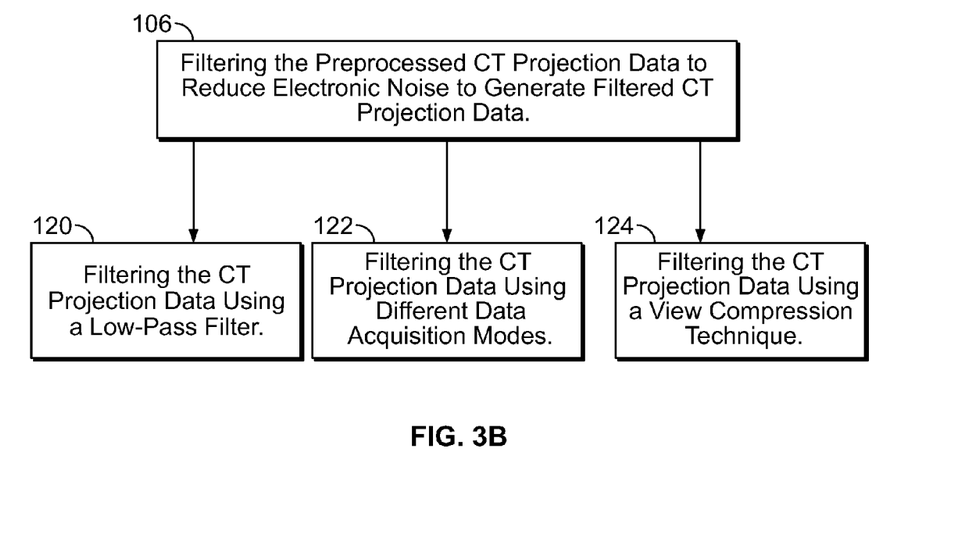

FIG. 3 is a flowchart illustrating an exemplary method 100 of correcting multi-modality imaging data. In the exemplary embodiment, the multi-modality imaging data may be PET or SPECT imaging data, for example. In the exemplary embodiment, method 100 includes generating 102 a plurality of computed tomography (CT) projection data and preprocessing 104 the CT projection data to generate preprocessed CT projection data. Method 100 also includes filtering 106 the preprocessed CT projection data to reduce electronic noise to generate filtered CT projection data, and performing 108 a minus logarithmic operation on the filtered CT projection data to generate the corrected CTAC data.

To generate a CT diagnostic quality image, method 100 includes adjusting 110 a tube current utilized by the CT imaging system to a second tube current to generate an attenuation correction map, the second tube current being less than the first tube current. More specifically the CT imaging system 11 is configured to generate CT quality diagnostic images when the tube current level is set to a first tube current that in the exemplary embodiment is between approximately 200 mA-400 mA. However, as discussed above, the resolution of the CT diagnostic quality images far exceeds the resolution required to create the CTAC. Method 100 therefore includes adjusting 110 or reducing 110 the level of the tube current to a value, referred to herein as an attenuation correction map (CTAC) value or a second tube current value, to generate an attenuation correction map, the second tube current being less than the first tube current value.

The CTAC value is less than the tube current setting value used to generate diagnostic quality CT images. For example, the second tube current value or attenuation correction map (CTAC) value is less than 20 mA. In the exemplary embodiment, the attenuation correction map (CTAC) value is between approximately 10 mA and approximately 20 mA. Setting the tube current to the attenuation correction map (CTAC) value facilitates reducing the overall x-ray dosage received by the patient 22 during scanning and also reducing the CT image resolution as will be discussed below. The method 100 further includes generating 102 a plurality of computed tomography (CT) projection data with the tube current set to the attenuation correction map (CTAC) value.

Method 100 also includes preprocessing 104 the CT projection data to generate preprocessed CT projection data. In the exemplary embodiment, preprocessing 104 the CT projection data includes applying 112 a detector gain-calibration, a reference channel normalization, and/or other corrections to the CT projection data. Optionally preprocessing 104 the CT projection data may also include applying a scatter correction or using various other techniques to preprocess the CT projection data.

Figure 4:
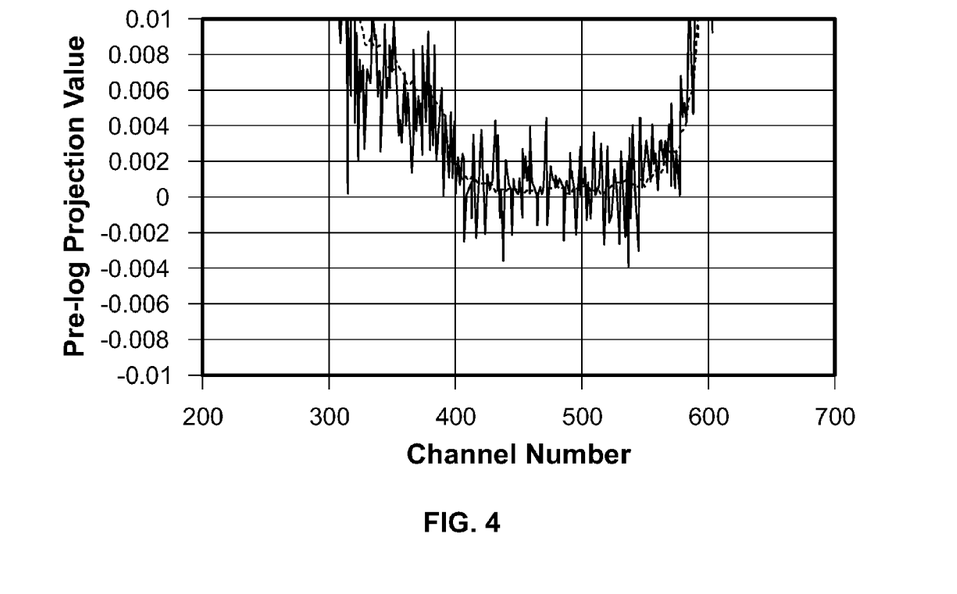
FIG. 4 is a graphical illustration of a set of CT projection values corresponding to a single detector row of a single projection view in accordance with an embodiment of the present invention.

As discussed above, reducing the tube current value or voltage value can result in negative signals. For example, FIG. 4 is a graphical illustration of a set of CT projection values corresponding to a single detector row of a single projection view of a body phantom. As shown in FIG. 4, when the x-ray tube current is set to the attenuation correction map (CTAC) value, a significant number of channels fall below zero. These negative values result in significant shading and streaking in the reconstructed images.

These negative values are caused by the presence of electronic noise in the CT DAS system 32. As discussed above, when the tube current is set to generate diagnostic quality images, i.e. a relatively high tube current, the relatively high tube current causes relatively high x-ray flux conditions to occur. Since the electronic noise is a small fraction of the fluctuation due to x-ray photon statistics, the electronic noise does not significantly impact the final projection reading. However, when the tube current is set to a value lower than would be used to produce CT images acceptable for diagnosis or anatomical localization, the x-ray flux is reduced, and the electronic noise becomes a significant portion of the overall noise resulting in the production of the negative values shown in FIG. 4. To reduce the impact of the electronic noise, method 100 further includes filtering 106 the preprocessed CT projection data to reduce the effect of electronic noise to generate filtered CT projection data.

Filtering to remove negative values that produce streaks in diagnostic quality images may be accomplished by replacing the negative value by an average of the pre-processed projection data of nearby detector channels. Replacing negative values causes the mean or average value to change and become more positive and the resulting data would appear less attenuating. For scans performed at lower tube currents this change results in CT numbers shifting lower and the CTAC values generated undercorrecting the PET data. To generate accurate CTAC data, the filtering or other processing used to remove negative values preserves the mean value. For example, in the N×N neighborhood of a negative projection data, the mean values before and after the filtering operation remains the same. Many filtering operators exhibit such characteristics and are described in the following paragraphs. Filters that meet such a requirement are called mean-preserving filters.

In the exemplary embodiment filtering 106 the preprocessed CT projection data to reduce electronic noise includes filtering 106 the preprocessed CT projection data using a low-pass filter prior to performing the minus-logarithmic operation on the CT projection data. The following equation represents an exemplary low-pass filter that may be used to filter the preprocessed projection data.

$$p'(\gamma,\beta,z) = -\log(p(\gamma,\beta,z) \otimes f(\gamma,\beta,z))  \quad \text{Equation 1}$$

wherein $\gamma$, $\beta$, and z denote the detector channel, view, and row indexes, respectively, and $f(\gamma,\beta,z)$ is a low-pass filter and $\otimes$ is a convolution operator.

In the exemplary embodiment, the filtering step 106 may be performed in many different locations prior to the minus logarithmic operation and after the detector gain-calibration has occurred. Specifically without detector gain-calibration, detector channel-to-channel gain variations are present in the projection signal and low-pass filtering operation may blend these variations in the filtered signal to produce ring artifacts in the final image. Smoothing of each dimension could be performed as soon as the appropriate calibrations have been applied to correct non-uniformities in that dimension. The view to view smoothing could be performed before or after detector gain-calibration, while the channel to channel smoothing should be performed after air-calibration. Performing the smoothing on each dimension independently may facilitate access to the appropriate data.

In use, filtering 106 the preprocessed projection data using a low-pass filter reduces spatial resolution. However, method 100 uses the mismatch between the spatial resolutions in the CT image and the PET image. As discussed above, the spatial resolution in CT is much higher than PET, and is well beyond the desired resolution for the attenuation map. As a result, performing 106 a filtering operation on the preprocessed CT projection data does not impact the accuracy of the final attenuation map. Rather, the spatial resolution of the CT images is purposely reduced using a reconstruction kernel and post-processing techniques.

In one embodiment, filtering the 106 the CT projection data to reduce electronic noise further includes filtering 120 the CT projection data using a three-dimensional boxcar filter. Using a low-pass filtering operation, boxcar smoothing, Equation (1) can be reduced to the following:

$$p'(\gamma, \beta, z) = -\log\left(\frac{1}{(2N+1)(2M+1)(2L+1)} \sum_{\Delta\gamma=-N}^{N} \sum_{\Delta\beta=-M}^{M} \sum_{\Delta z=-L}^{L} p(\gamma+\Delta\gamma, \beta+\Delta\beta, z+\Delta z)\right) \quad \text{Equation 2}$$

wherein γ, β, and z denote the detector channel, view, and row indexes, respectively, and p'(γ, β, z) is a three-dimensional low-pass boxcar filter that performs averaging or filtering across the views, rows, and channels dimensions, and N, M, and L are the boxcar filter parameters. These parameters can be determined a prior based on the scanning techniques and scanned object, or can be determined dynamically based on the amount of negative values present in the projection.

Optionally, filtering 106 the CT projection data includes filtering 120 the projection using a wider kernel such a three-dimensional low-pass boxcar filter that performs 5×5×5, or 5×3×5 or 3×1×3 averaging or filtering independently across the views, rows, and channels dimensions respectively. For example, the exemplary filter may be a 3×1 filter in the view direction, a 5×1 filter in the row direction, and a 3×3 filter in the channel direction. In the exemplary embodiment, filtering 120 the CT projection data includes using any size low-pass filter, kernel coefficients, such as with a weighted average, and/or any other desired low-pass filter and may have different kernels in each dimension. In the exemplary embodiment, additional filtering is applied to the filtered data if negative values are still observed in the resulting signal.

In another embodiment filtering 106 the CT projection data includes filtering 122 the CT projection data using different data acquisition modes available on the CT scanner to perform the equivalent operation as is performed in method 120. In the exemplary embodiment, filtering 122 includes acquiring the data CT projection data over thicker rows of the detector and averaging the electronic noise over multiple input channels. For example, a 16×1.25 mm detector can be configured as a 16×1.25 mm detector, an 8×2.5 mm detector, or a 4×3.75 mm detector. In this embodiment, filtering 122 includes acquiring the CT projection data using an 8×2.5 or 4×3.75 mm detector configuration. Since the analogue detector signals are summed in a front-end-processor prior to the pre-processing step 104, and thus prior to performing 108, the minus logarithmic operation, the row-wise filtering is achieved without the separate processing after data acquisition is complete. In the exemplary embodiment, the analogue signal generated using the 4×3.75 detector configuration is approximately three times greater than the analog signal generated using the 16×1.25 detector configuration that is approximately equivalent to averaging using a kernel length of 3 in the row dimension as discussed above. Moreover, acquiring data using the 16×1.25 mm detector configuration uses a full 20 mm of the detector array 18, whereas acquiring data using the 4×3.75 mm detector configuration uses only 15 mm of the detector array 18. Optionally the CT projection data may be acquired using a 8×2.5 mm detector configuration. The 8×2.5 mm detector configuration uses the full 20 mm of the detector array 18 that is approximately equivalent to averaging using a kernel length of 2 in the row dimension as discussed above producing an analog signal that is approximately twice that of the 16×1.25 mm detector array configuration.

Using a detector configuration that is different than the 16×1.25 mm detector configuration that uses a full 20 mm of the detector array 18, provides a more efficient method of filtering the CT projection data. For example, projection samples from different detector rows are processed by different processors and there is little communication pathway between these processors. As a result, it is more time consuming to perform averaging or low-pass filtering across either of the detector rows, detector channels, or projection views. However, using the 4×3.75 mm detector configuration, or other optional detector configurations discussed above, allows the imaging system to process the CT projection data using data that is acquired in the same view and row, thus increasing the efficiency in performing averaging or low-pass filtering across the detector channels. In another embodiment the detector channels are ganged across the detector arc to produce projections of coarser spatial resolution. For example, two neighboring channels are combined electronically to enable 444 channels by 64 rows data collection instead of the nominal 888 channels by 64 rows. This approach can further combined with the detector row configuration to result in a 444 channels by 16 rows data samples per view. Of course, other detector configuration combinations are also possible.

In another embodiment filtering 106 the CT projection data includes filtering 124 the CT projection data using a view compression technique. In the exemplary embodiment view compression is a mode wherein the gantry rotates slower than for a normal acquisition to generate a number of views per rotation that is an integer number of times that of a normal acquisition. During the pre-processing step 104, these views are averaged before the negative logarithm is applied to reduce noise in the reconstructions. In the exemplary embodiment for the purposes of low-dose CT for PET attenuation correction, the CT projection views are acquired using the same gantry speed (i.e. the same number of views as is used to generate the CT diagnostic quality images. Additionally the number of views is reduced prior, using the view compression technique, to average the electronic noise component of the signal before negative logarithm is applied. In use, the view compression technique applies a view compression factor to the CT projection data. In the exemplary embodiment the view compression factor is 3:1, an equivalent effect to that of filtering across the views with a kernel length of 3, as discussed above, is thus achieved. Method 100 therefore facilitates generating accurate CT Hounsfield Unit values while scanning the patient with a low dose x-ray. In another embodiment of the present invention, the DAS (data acquisition system) sampling rate is changed so that it is slower than the diagnostic CT data collection sampling rate. For example, for one second gantry rotation speed, the DAS sampling rate is reduced to 500 Hz instead of 1000 Hz so that the number of x-ray photons per sample is increased.

After the preprocessed CT projection data has been filtered to reduce electronic noise, method 100 also includes performing 108 a minus logarithmic operation on the filtered CT projection data. In the exemplary embodiment, the minus logarithmic step includes additional processing such as taking the absolute value of projection value to eliminate any negative detector signals. Alternatively, a mean-preserving filter can be applied so that the average signal after the logarithmic operation is substantially unchanged. The mean-preserving filter will assign the negative sample value to a predetermined value while changing the values of its neighbors at the same time to keep the mean values substantially the same. Alternatively, a dynamically calculated value can be used to replace the negative value instead of a predetermined value, and neighboring channel values are modified accordingly. The processed projection data can then be fed through other preprocessing and reconstruction steps to arrive at a reconstructed image.

The method and apparatus described herein facilitates generating attenuation correction data that can be utilized to remove the effects of attenuation and scatter from a PET image. Specifically, the methods and apparatus described herein facilitate reducing patient motion induced image artifacts while also reducing the reducing the X-ray dosage delivered to a patient. To overcome shading and other imaging problems generally associated with low-dose radiation imaging, the method also includes filtering the CT projection data prior to performing the minus logarithmic operation to reduce the negative projection values that occur as a result of electronic noise in the CT data acquisition system.

While the invention has been described in terms of various specific embodiments, those skilled in the art will recognize that the invention can be practiced with modification within the spirit and scope of the claims.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the tapes of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method for correcting multi-modality imaging data, said method comprising:
adjusting a tube current of a computed tomography (CT) imaging system to a first tube current value sufficient to generate an attenuation correction map, the first tube current value being less than a second tube current value used to generate diagnostic quality CT images;
generating, at the first tube current value, a plurality of computed tomography (CT) projection data using the CT imaging system, wherein the first tube current value has an associated x-ray flux that produces negative values in the CT projection data,
preprocessing the CT projection data to generate preprocessed CT projection data;
filtering the preprocessed CT projection data to reduce the effect of electronic noise to generate filtered CT projection data; and
performing a minus logarithmic operation on the filtered CT projection data to convert the negative values to positive values to generate corrected positron emission tomography (PET) data.

2. A method in accordance with claim 1 wherein filtering the preprocessed CT projection data further comprises filtering the CT projection data using a low-pass filter.

3. A method in accordance with claim 1 wherein filtering the preprocessed CT projection data further comprises applying a weighted average filter independently across the channel, row, and view directions.

4. A method in accordance with claim 1 wherein filtering the preprocessed CT projection data further comprises:
filtering the CT projection data in a first direction;
filtering the CT projection data in a second direction that is different than the first direction; and
filtering the CT projection data in a third direction that is different than the second direction.

5. A method in accordance with claim 1 wherein filtering the preprocessed CT projection data further comprises filtering the CT projection data using a mean-preserving filter.

6. A method in accordance with claim 1 wherein filtering the preprocessed CT projection data further comprises filtering the preprocessed CT projection data by electronically combining analog signals generated from neighboring detector channels, rows, and views.

7. A method in accordance with claim 1 wherein filtering the preprocessed CT projection data further comprises filtering the preprocessed CT projection data using a filtering parameter that is dynamically adjusted based on the quantity of negative values in the preprocessed CT projection data.

8. A method in accordance with claim 1 wherein filtering the preprocessed CT projection data further comprises filtering the preprocessed CT projection data using a mean-preserving filter to reduce the quantity of negative values in the preprocessed CT projection data.

9. A method in accordance with claim 1 wherein filtering the preprocessed CT projection data further comprises:
   acquiring the CT projection data using a 4×3.75 millimeter detector configuration; and
   filtering the preprocessed CT projection data to reduce electronic noise.

10. A method in accordance with claim 1 wherein filtering the preprocessed CT projection data further comprises applying a 3:1 view compression factor to the CT projection data.

11. A multi-modality imaging system comprising a first modality unit, a second modality unit, and a computer operationally coupled to the first and second modality units, wherein the computer is programmed to:
   adjust a tube current of a computed tomography (CT) imaging system to a first tube current value sufficient to generate an attenuation correction map, the first tube current value being less than a second tube current value used to generate diagnostic quality CT images;
   generate a plurality of CT projection data from the CT imaging system, wherein the first tube current value has an associated x-ray flux that produces negative values in the CT projection data,
   preprocess the CT projection data to generate preprocessed CT projection data;
   filter the preprocessed CT projection data to reduce the effect of electronic noise to generate filtered CT projection data; and
   perform a minus logarithmic operation on the filtered CT projection data to convert the negative values to positive values to generate at least one of corrected positron emission tomography (PET) data or corrected Single Photon Emission Computed Tomography (SPECT) data.

12. A multi-modality imaging system in accordance with claim 11, wherein the computer is further programmed to apply a weighted average filter independently across the channel, row, and view directions to filter the preprocessed CT projection data.

13. A multi-modality imaging system in accordance with claim 11, wherein the computer is further programmed to filter the preprocessed CT projection data using a low-pass boxcar filter.

14. A multi-modality imaging system in accordance with claim 11, wherein the computer is further programmed to filter the preprocessed CT projection data using a three-dimensional low-pass boxcar filter.

15. A multi-modality imaging system in accordance with claim 11, wherein the computer is further programmed to acquire the CT projection data using a 4×3.75 millimeter detector configuration.

16. A multi-modality imaging system in accordance with claim 11, wherein the computer is further programmed to apply a 3:1 view compression factor to the CT projection data.

17. A non-transitory computer readable medium encoded with a program programmed to instruct a computer to:
   adjust a tube current of a computed tomography (CT) imaging system to a first tube current value sufficient to generate an attenuation correction map, the first tube current value being less than a second tube current value used to generate diagnostic quality CT images;
   generate a plurality of CT projection data from the CT imaging system, wherein the first tube current value has an associated x-ray flux that produces negative values in the CT projection data,
   preprocess the CT projection data to generate preprocessed CT projection data;
   filter the preprocessed CT projection data to reduce electronic noise to generate filtered CT projection data; and
   perform a minus logarithmic operation on the filtered CT projection data to convert the negative values to generate corrected at least one of corrected positron emission tomography (PET) data or corrected Single Photon Emission Computed Tomography (SPECT) data.

18. A non-transitory computer readable medium in accordance with claim 17 wherein the program is further programmed to instruct the computer to use a filtering parameter that is dynamically adjusted based on the quantity of negative values in the preprocessed CT projection data.

19. A non-transitory computer readable medium in accordance with claim 17 wherein the program is further programmed to instruct the computer to filter the preprocessed CT projection data using a three-dimensional low-pass boxcar filter.

20. A non-transitory computer readable medium in accordance with claim 17 wherein the program is further programmed to instruct the computer to acquire the CT projection data using a 4×3.75 millimeter detector configuration.

21. A method in accordance with claim 1, wherein the first tube current value is between approximately 10 mA and approximately 20 mA.

22. A method in accordance with claim 1, wherein preprocessing the CT projection data comprises applying a detector gain calibration, a reference channel normalization, or a scatter correction to the CT projection data.

23. A method in accordance with claim 1, wherein the first tube current value is less than 20 mA.

24. A method in accordance with claim 1, wherein the second first tube current is approximately ten times greater than the first tube current value.

* * * * *